US006551264B1

(12) United States Patent
Cawley et al.

(10) Patent No.: US 6,551,264 B1
(45) Date of Patent: Apr. 22, 2003

(54) ORTHOSIS FOR DYNAMICALLY STABILIZING THE PATELLO-FEMORAL JOINT

(75) Inventors: Patrick W. Cawley, Carlsbad, CA (US); Michael Meritt-Powell, Oceanside, CA (US); Jeffrey T. Mason, Escondido, CA (US)

(73) Assignee: Breg, Inc., Vista, CA (US)

( * ) Notice: Subject to any disclaimer, the term of this patent is extended or adjusted under 35 U.S.C. 154(b) by 134 days.

(21) Appl. No.: 09/669,061

(22) Filed: Sep. 22, 2000

(51) Int. Cl.[7] .................................................. A61F 5/00
(52) U.S. Cl. ............................ 602/16; 602/26; 128/882
(58) Field of Search .............................. 602/26, 62, 16, 602/23, 60, 61, 63, 5; 128/882

(56) References Cited

U.S. PATENT DOCUMENTS

| 4,201,203 | A |   | 5/1980  | Applegate ..................... 128/80 |
| 4,296,744 | A | * | 10/1981 | Palumbo ...................... 602/26 |
| 4,370,978 | A |   | 2/1983  | Palumbo ...................... 128/80 |
| 4,423,720 | A |   | 1/1984  | Meier et al. ................. 128/80 |
| 4,425,912 | A |   | 1/1984  | Harper ........................ 128/80 |
| 4,445,505 | A |   | 5/1984  | Labour et al. ................ 128/80 |
| 4,466,428 | A |   | 8/1984  | McCoy ........................ 128/80 |
| 4,506,661 | A | * | 3/1985  | Foster ........................ 602/26 |
| 4,572,170 | A | * | 2/1986  | Cronk et al. ................. 602/26 |
| 4,607,628 | A |   | 8/1986  | Dashefsky .................... 128/80 |
| 4,681,097 | A | * | 7/1987  | Pansiera ...................... 128/77 |
| 4,854,308 | A |   | 8/1989  | Drillo ........................ 128/80 |
| 4,872,448 | A |   | 10/1989 | Johnson, Jr. ................. 128/80 |
| 4,991,571 | A | * | 2/1991  | Kausek ........................ 602/26 |
| 5,024,216 | A |   | 6/1991  | Shiono ........................ 128/80 |
| 5,277,697 | A | * | 1/1994  | France et al. ................ 606/16 |
| 5,288,287 | A | * | 2/1994  | Castillo et al. .............. 602/16 |
| 5,556,374 | A |   | 9/1996  | Grace et al. ................. 602/26 |
| 5,613,943 | A |   | 3/1997  | Palumbo ...................... 602/62 |
| 5,759,167 | A |   | 6/1998  | Shields, Jr. et al. .......... 602/26 |
| 5,797,864 | A |   | 8/1998  | Taylor ........................ 602/26 |
| 5,807,298 | A |   | 9/1998  | Palumbo ...................... 602/62 |
| 5,857,988 | A |   | 1/1999  | Shirley ....................... 602/26 |
| 5,865,776 | A |   | 2/1999  | Springs ....................... 602/26 |
| 5,873,848 | A |   | 2/1999  | Fulkerson .................... 602/62 |
| RE37,297  | E | * | 7/2001  | Smith, III .................... 602/26 |

* cited by examiner

*Primary Examiner*—Kevin Shaver
*Assistant Examiner*—David C Comstock
(74) *Attorney, Agent, or Firm*—Rodney F. Brown

(57) ABSTRACT

An orthosis is provided which is mountable on a knee having a femoral head and patella. The orthosis has upper and lower arms positionable about the knee and a hinge assembly positioned between the upper and lower arms at the knee to one side of the patella. A compression member is positioned at the femoral head adjacent to the patella on the opposite side of the patella from the hinge assembly. The compression member includes a tracking guide engaging the knee and a compression place in overlying engagement with the tracking guide. A tension strap is connected to the hinge assembly at an offset connection point by means of a tension strap mount. The tension strap applies a tension force to the compression member which increases when the upper and lower arms rotatably transition from the flexion position to the extension position and decreases when the upper and lower arms rotatably transition from the extension position to the flexion position.

35 Claims, 9 Drawing Sheets

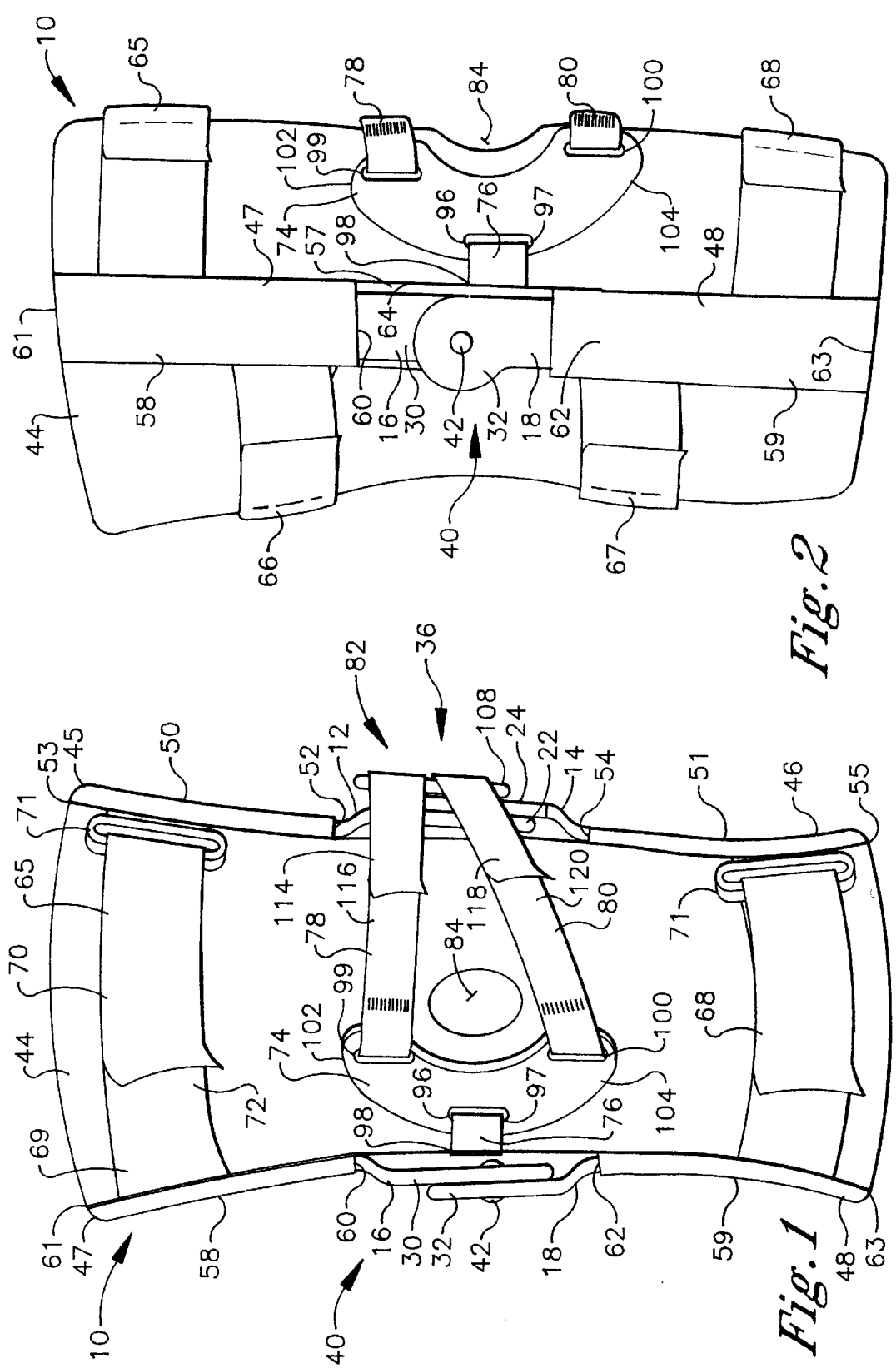

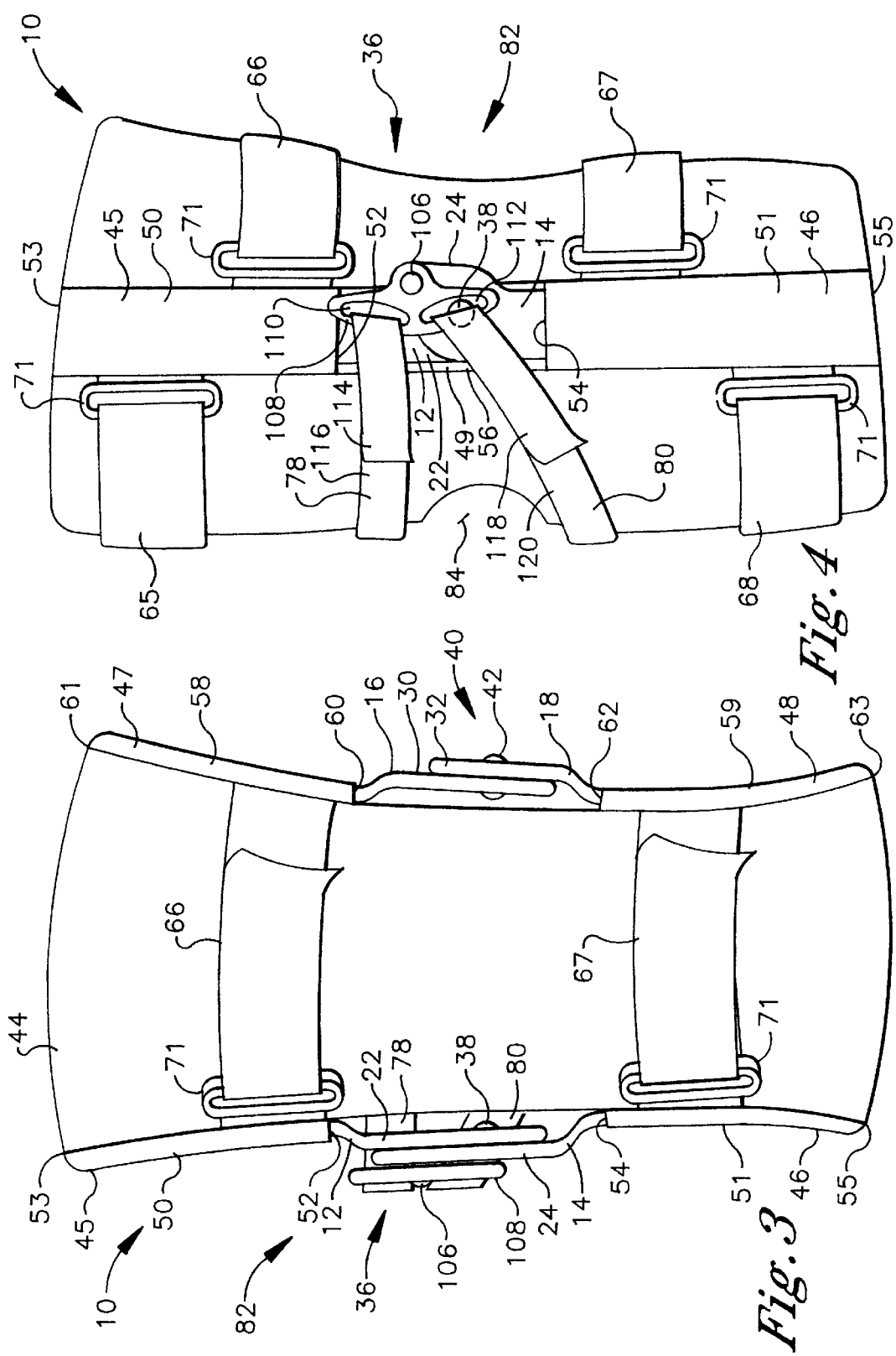

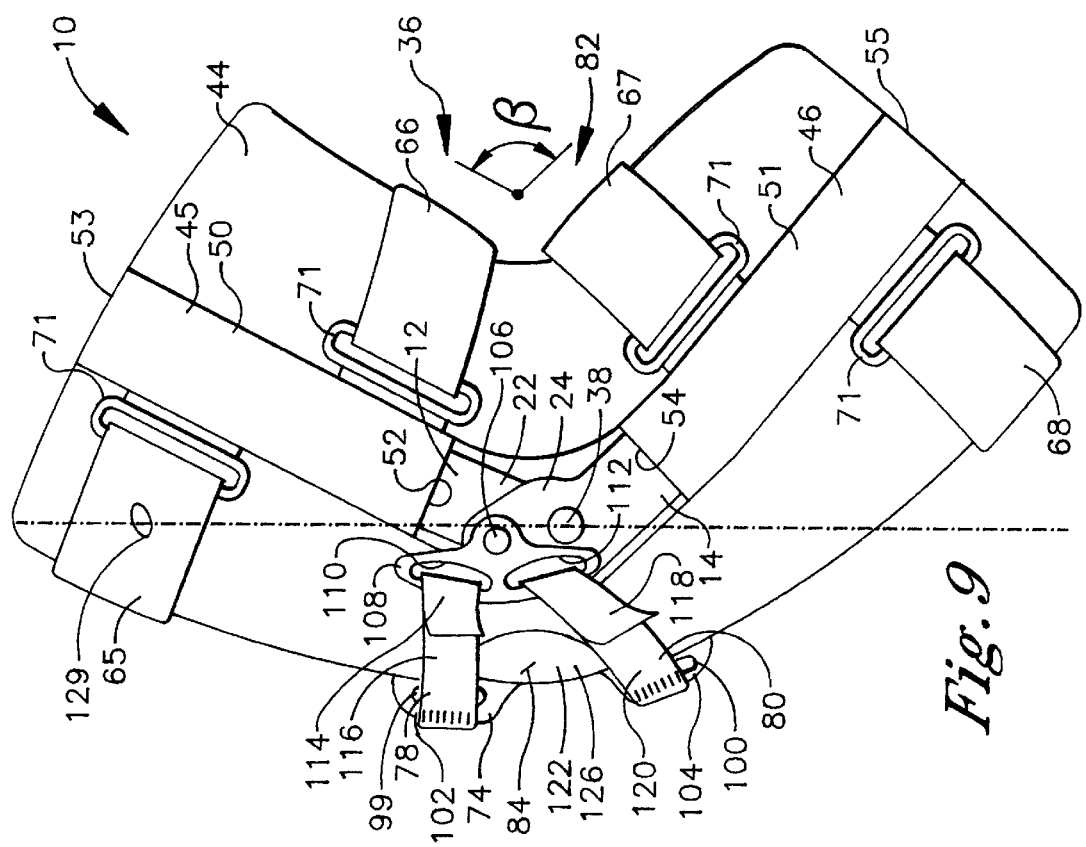
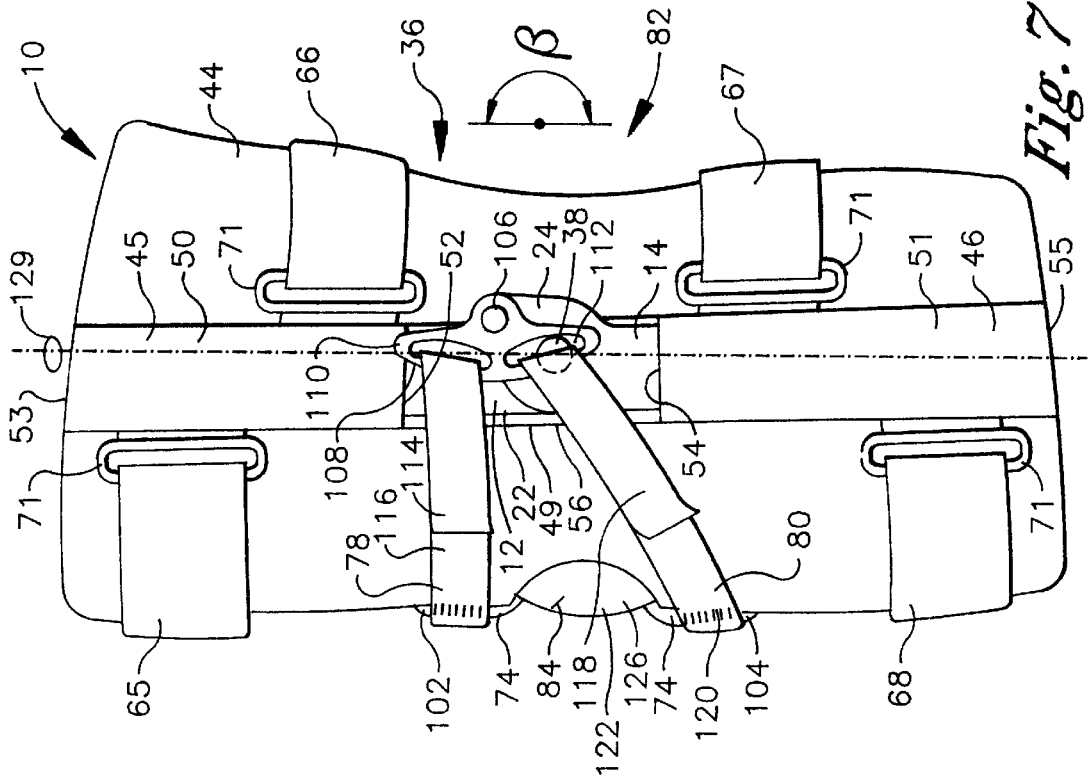
Fig. 9
Fig. 7

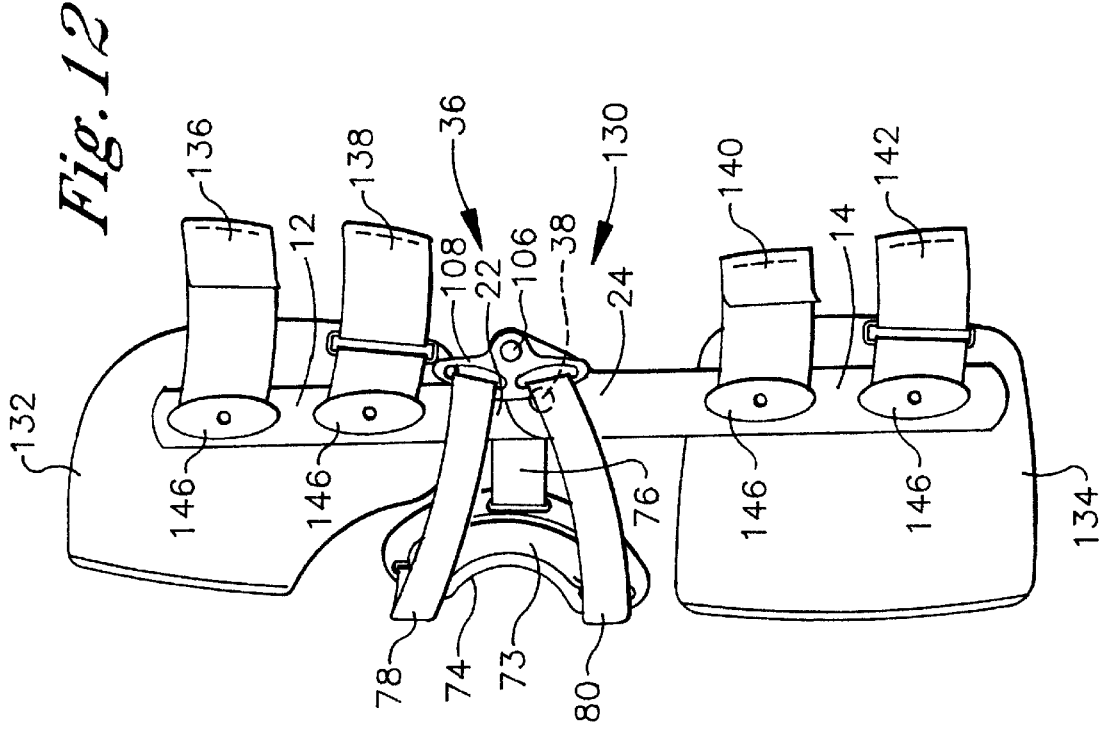
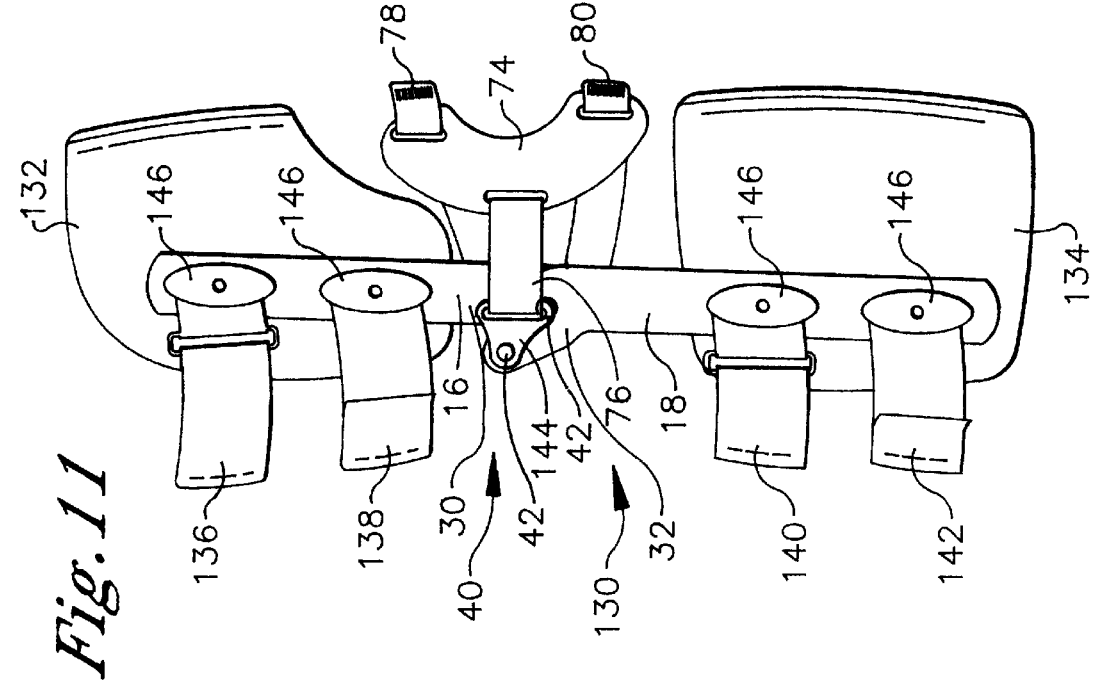

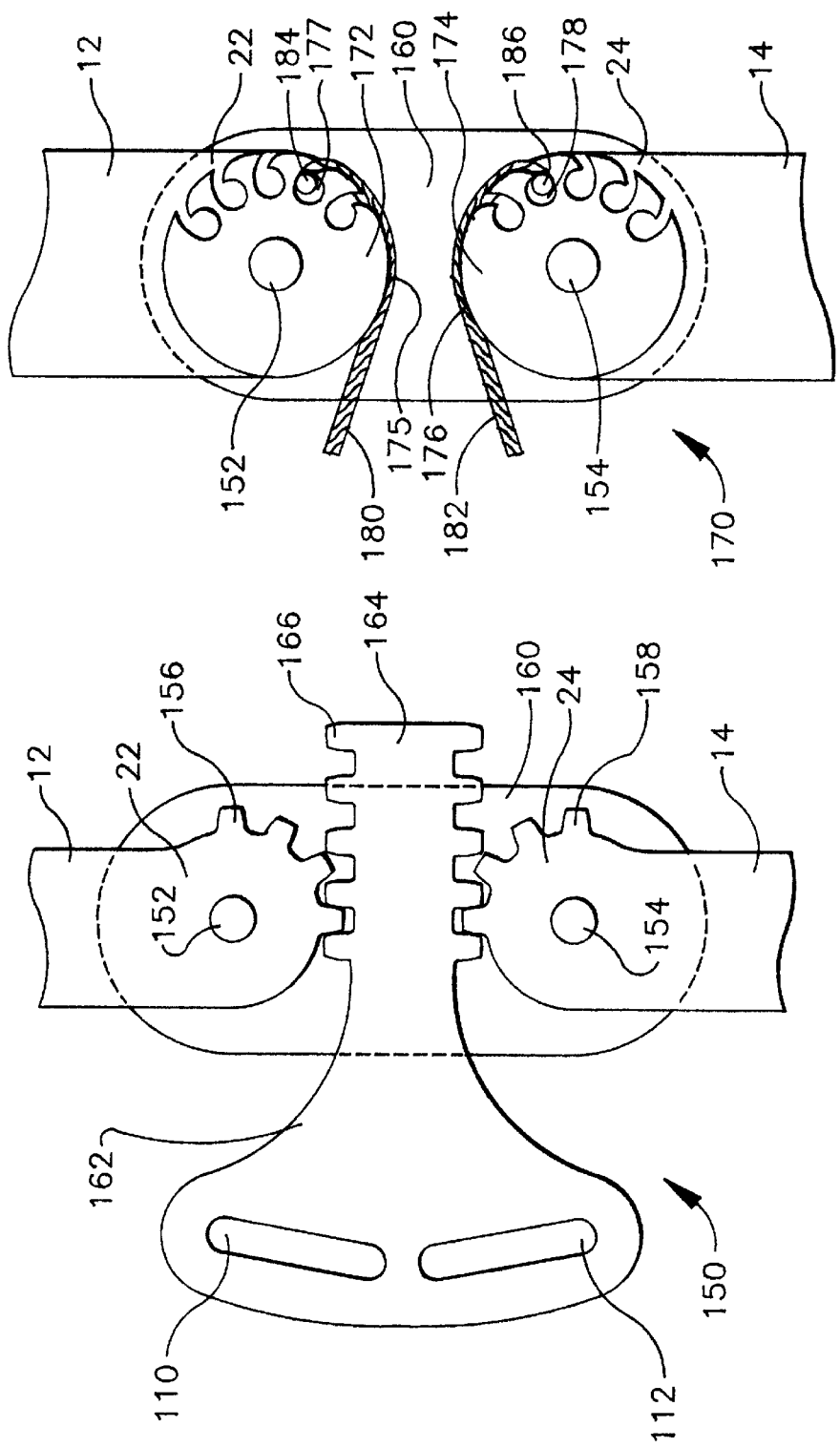

ORTHOSIS FOR DYNAMICALLY STABILIZING THE PATELLO-FEMORAL JOINT

TECHNICAL FIELD

The present invention relates generally to knee orthoses, and more particularly to a knee orthosis which causes the patella to properly track the trochlear groove during movement of the knee.

BACKGROUND OF THE INVENTION

The patello-femoral joint of the knee is an articulation between the patella and femur. The joint consists of an articular surface on the posterior of the patella and a corresponding articular surface on the anterior of the head of the femur which is termed the trochlea. The posterior of the patella is contoured as a ridge, while the trochlea is contoured as a groove which is dimensioned to receive the patellar ridge in a complementary manner. Proper dynamic function of the patello-femoral joint requires that the patellar ridge accurately track the underlying trochlear groove when the knee is moved through flexion or extension. The anatomy and function of the patello-femoral joint are well known and described in detail in Ficat, R. P. et al., *Disorders of the Patello-femoral Joint*, Williams & Wilkins, 1977.

Functional disorders of the patello-femoral joint frequently relate to improper dynamics. Less severe forms of patello-femoral joint disorder cause pain in the joint, but do not exhibit errors in patellar tracking of the trochlear groove. In more severe forms of patello-femoral joint disorder, patellar tracking errors are evident in addition to joint pain, but there is no subluxation or dislocation of the joint. In still more severe forms of patello-femoral joint disorder, patellar tracking errors result in subluxation or dislocation of the joint. Recurrent subluxation of the patello-femoral joint is a particular disorder whereby the patella deviates transiently and typically rapidly from its normal axis of movement due to patellar tracking errors during movement of the knee. Slight deviations of the-patella from its normal axis of movement are termed minor subluxation and may not produce any clinically apparent relocation of the patella. Minor subluxation is often the result of a functional imbalance in the knee. Significant deviations of patellar movement which approach dislocation are termed major subluxation. Major subluxation can be brought on by strenuous activity although it often occurs even in the absence of such activity. Recurrent patellar subluxation both major and minor, is a relatively frequent condition among women generally and particularly among women athletes.

Most instances of subluxation or dislocation of the patella due to patellar tracking errors are in the lateral direction because biomechanical forces typically bias the patella laterally when the knee is load-bearing. In addition, subluxation or dislocation of the patella due to patellar tracking errors has the greatest risk of occurring when the knee is approaching extension. When the knee ranges between about 30° of full extension and full extension, the trochlear groove becomes relatively small and shallow which is conducive to subluxation or dislocation. Functional disorders of the patello-femoral joint are highly undesirable because such disorders may ultimately lead to cartilage damage and arthritis of the knee. Therefore, a recognized need exists for effective preventative or remedial treatment of patello-femoral joint disorders.

It is an object of the present invention to provide a knee orthosis which prevents or remediates functional disorders of the patello-femoral joint including recurrent patellar subluxation or dislocation. More particularly it is an object of the present invention to provide a knee orthosis which reduces the risk of patellar tracking errors by providing the knee with a patellar tracking guide. It is a specific object of the present invention to provide a knee orthosis which applies a patellar tracking guide to the head of the femur laterally or medially adjacent to the patella to reduce the risk of recurrent lateral or medial patellar subluxation or dislocation. It is a further object of the present invention to provide a knee orthosis having a patellar tracking guide which dynamically tensions when the knee approaches the extension position for maximum effect and dynamically relaxes when the knee approaches the flexion position to minimize interference with the function of the knee. It is still a further object of the present invention to provide a knee orthosis having a patellar tracking guide which is dynamically positioned more proximal to the patella when the knee approaches the extension position for maximum effect and is dynamically positioned more distal to the patella when the knee approaches the flexion position to minimize interference with the function of the knee. These objects and others are accomplished in accordance with the invention described hereafter.

SUMMARY OF THE INVENTION

The present invention is an orthosis mountable on a knee having a femoral head and patella. The orthosis comprises first upper and lower arms positionable about the knee and a first hinge assembly positioned between the first upper and lower arms at the knee to one side of the patella. The first hinge assembly includes a lower end of the first upper arm, an upper end of the first lower arm and a pivot rotationally engaging the lower and upper ends of the first upper and lower arms, respectively. The first upper and lower arms are rotatable about the pivot to transition between a flexion position and an extension position. The orthosis further comprises second upper and lower arms and a second hinge assembly, which are substantially the same as the first arms and first hinge assembly, but are positioned at the knee to the opposite side of the patella from the first arms and first hinge assembly. A substantially-flexible tubular sleeve is provided to retain the upper and lower arms in relation to the knee. Alternatively, a stiffened upper cuff is provided to retain the upper arms and a stiffened lower cuff is provided to retain the lower arms.

A compression member is positioned at the femoral head adjacent to the patella on the opposite side of the patella from the first hinge assembly. In accordance with one embodiment, the compression member comprises a tracking guide engaging the knee and a compression plate in overlying engagement with the tracking guide. The compression plate is formed from a substantially more rigid material than the relatively pliant tracking guide. A tension strap is connected to the first hinge assembly at a first connection paint by means of a tension strap mount. In accordance with one embodiment, the tension strap mount includes a pivot and a mounting plate. The pivot of the tension strap mount is spatially offset from the pivot of the first hinge assembly and rotatably connects the mounting plate to the lower end of the first upper arm or to the upper end of the first lower arm. The tension strap is additionally connected to the compression member at a second connection point which is on the compression plate.

When the first upper and lower arms rotatably transition from the flexion position to the extension position, the first connection point is posteriorly displaced relative to the hinge pivot to position the compression member more proximal to the patella while increasing the tension force applied to the compression member. Conversely, when the first upper and lower arms rotatably transition from the extension position to the flexion position, the first connection point is anteriorly displaced relative to the hinge pivot to position the compression member more distal to the patella while decreasing the tension force applied to the compression member. The orthosis is further provided with a counterbalance connector connected to the compression member and oriented counter to the tension strap.

The present orthosis enables a method for maintaining proper tracking of the patella relative to the femoral head during range of motion movement of the knee. The method is initiated by placing the compression member in engagement with the knee at a location on the femoral head adjacent to the patella. The compression member is aligned with a desired dynamic patellar track. Range of motion movement is then performed on the knee by moving the knee from a flexion position to an extension position or from an extension position to a flexion position while applying a tension force to the compression member by the tension strap. The tension force is increased and the compression member is drawn closer to the patella when the knee approaches the extension position. Conversely, the tension force is decreased and the compression member is drawn away from the patella when the knee approaches the flexion position. As such, the compression member presses against the femoral head with a variable tension force and is dynamically positioned relative to the patella which enables the compression member to conform the patella to the desired dynamic patellar track during movement of the knee.

The present invention will be further understood from the drawings and the following detailed description.

BRIEF DESCRIPTION OF THE DRAWINGS

FIG. 1 is an anterior view of a knee orthosis of the present invention.

FIG. 2 is a lateral view of the knee orthosis of FIG. 1.

FIG. 3 is a posterior view of the knee orthosis of FIG. 1.

FIG. 4 is a medial view of the knee orthosis of FIG. 1.

FIG. 7 is a medial view of the knee orthosis of FIG. 1 operatively positioned on the knee of a user with the knee in the extension position.

FIG. 9 is a medial view of the knee orthosis of FIG. 1 operatively positioned on the knee of a user with the knee in the flexion position.

FIG. 11 is a lateral view of an alternate embodiment of a knee orthosis of the present invention.

FIG. 12 is a medial view of the knee orthosis of FIG. 11.

FIG. 13 is a medial view of an alternate embodiment of a hinge assembly and associated patellar tracking assembly having utility in a knee orthosis of the present invention.

FIG. 14 is a medial view of another alternate embodiment of a hinge assembly and associated patellar tracking assembly having utility in a knee orthosis of the present invention.

DESCRIPTION OF PREFERRED EMBODIMENTS

Figure 5:
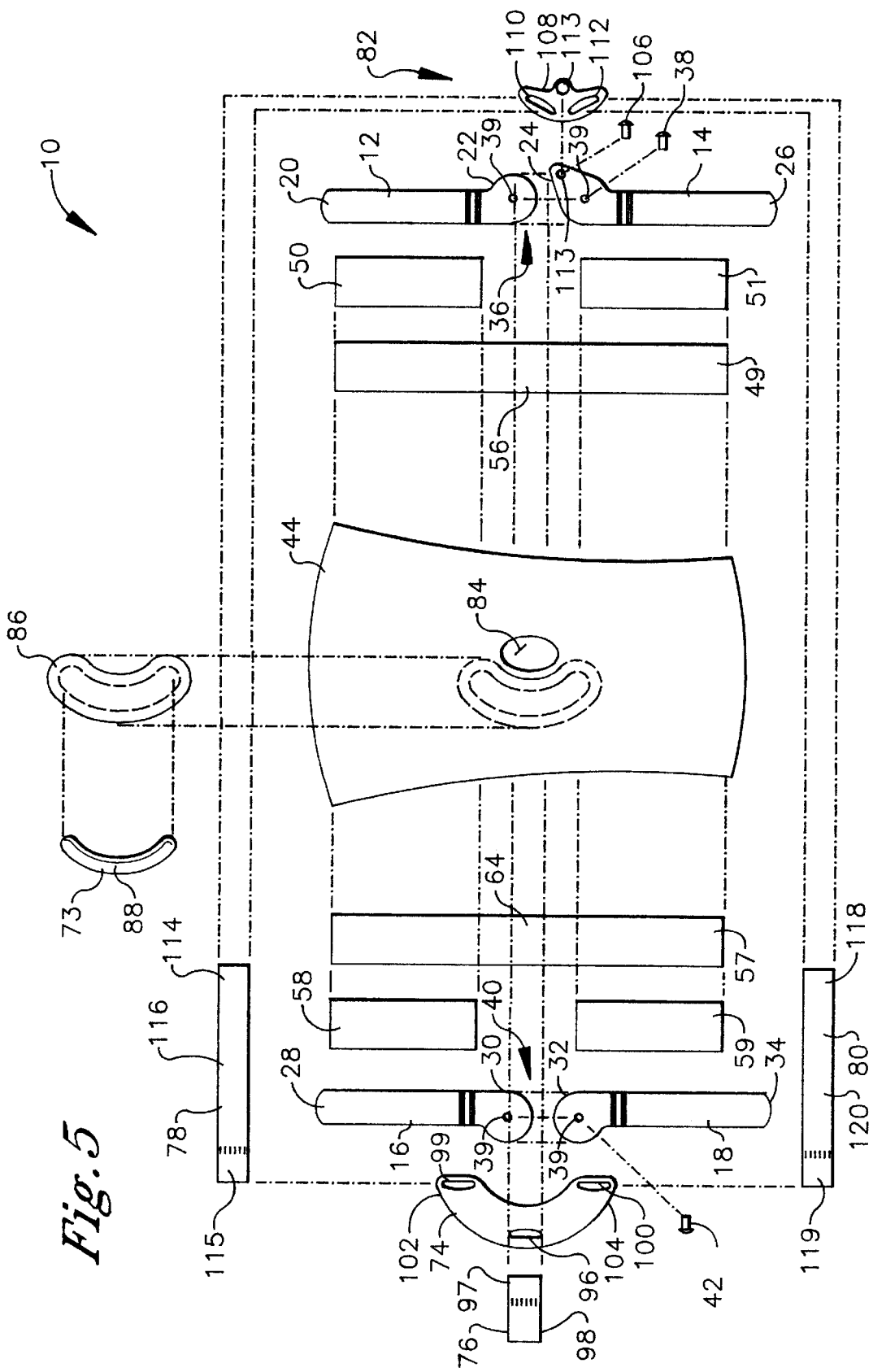
FIG. 5 is an exploded anterior view of the knee orthosis of FIG. 1 having the circumferential straps omitted for clarity of illustration.

Referring to FIGS. 1–5, the knee orthosis of the present invention is shown and generally designated 10. The positional terms upper, lower, lateral, medial, anterior and posterior, are used herein with refer to the normal orientation of a knee on which the knee orthosis 10 is mounted in practice as described hereafter.

The knee orthosis 10 has a first pair of arms positioned on one side of the orthosis 10 and a second pair of arms positioned on the opposite side of the orthosis 10. The first pair of arms consists of a first upper arm 12 and a first lower arm 14. The second pair consists of a second upper arm 16 and a second lower arm 18. The first upper arm 12 defines an upper end 20 and a lower end 22, the first lower arm 14 defines an upper end 24 and a lower end 26, the second upper arm 16 defines an upper end 28 and a lower end 30, and the second lower arm 18 defines an upper end 32 and a lower end 34. The arms 12, 14, 16, 18 have a bar-shaped configuration which provides the arms 12, 14, 16, 18 with semi-rigid flexibility characteristics. In particular the arms 12, 14, 16, 18 have a relatively larger dimension of width providing substantial inflexibility in the anterior and posterior directions and have a relatively smaller dimension of thickness providing a degree of flexibility in the medial and lateral direction. As such, each arm 12, 14, 16, 18 may be formed from the following types of materials which are well-known to those skilled in the art of hinged orthopedic knee braces: metals, fiberglass, graphite, resins, plastics, composites and combinations thereof. A preferred material is a glass-filled nylon.

The first pair of arms 12, 14 is provided with a first hinge assembly 36 which rotatably connects the first upper arm 12 and the first lower arm 14 to one another. The first hinge assembly 36 includes the lower end 22 of the first upper arm 12, the upper end 24 of the fist lower arm 14, and a hinge pivot 38 which rotationally engages the overlapping lower and upper ends 22, 24. The overlap of the lower and upper ends 22, 24 renders the first hinge assembly 36 substantially rigid, although the upper and lower ends 20, 26 extended away from the first hinge assembly 36 remain semi-rigid, having a limited degree of flexibility as described above. The hinge pivot 38 shown herein is a single pivot element in the form of a rivet positioned within cooperatively aligned apertures 39 extending through the lower and upper ends 22, 24. Although not shown, the first hinge assembly 36 may additionally be provided with a conventional extension stop to substantially prevent rotation of the first hinge assembly 36 past a rotation angle of about 170°. As a result, the knee is not permitted to extend past about the final 10° of extension, thereby reducing the risk hyperextension of the knee when the knee orthosis 10 is operational as described hereafter.

The second pair of arms 16, 18 is likewise provided with a second hinge assembly 40 which rotatably connects the second upper arm 16 and the second lower arm 18 to one another. The second hinge assembly 40 includes the lower end 30 of the second upper arm 16, the upper end 32 of the second lower arm 14, and a hinge pivot 42 which rotationally engages the overlapping tower and upper ends 30, 32. The overlap of the lower and upper ends 30, 32 renders the second hinge assembly 40 substantially rigid, although the upper and lower ends 28, 34 extending away from the second hinge assembly 40 remain semi-rigid, having a limited degree of flexibility as described above. The hinge pivot 42 of the second hinge assembly 40 is substantially the same as the hinge pivot 38 of the first hinge assembly 36. Although not shown the second hinge assembly 40 may also be provided with a conventional extension stop substantially the same as that of the first hinge assembly 36.

It is understood that the above-recited embodiment of the first and second hinge assemblies 36, 40 is but one embodiment of a hinge assembly having utility herein. Alternate hinge assemblies are within the purview of the skilled artisan and may be utilized in the knee orthosis of the present invention. For example, a hinge assembly as disclosed in commonly-owned U.S. Pat. No. 5,807,294, incorporated herein by reference, is an alternate embodiment of a hinge assembly having utility in the knee orthosis of the present invention. The hinge assembly of U.S. Pat. No. 5,807,294 has a hinge pivot which includes a separate pivot element for each upper and lower arm such that the upper and lower arms do not overlap one another at the hinge pivot. Cooperative rotation of the upper and lower arms at the hinge pivot is enabled by intermeshing teeth on each arm.

The knee orthosis 10 has a tubular sleeve 44 formed from an elastic material, such as a breathable or non-breathable fabric-covered foam. The elastic sleeve 44 is highly flexible and stretchable, flexing and stretching to conform to the contours of a knee over which the sleeve 44 is fitted as described hereafter. The radial inwardly-directed elastic compression force of the sleeve 44 resists displacement of the sleeve 44 relative to the knee when the sleeve 44 is fitted over the knee. The sleeve 44 is provided with first arm pockets 45, 46 and second arm pockets 47, 48 parallely aligned with the longitudinal axis of the sleeve 44. The first arm pockets 45, 46 are sized and positioned to engage and enclose the upper end 20 of the first upper arm 12 and the lower end 26 of the first lower arm 14, respectively. The second arm packets 47, 48 are sized and positioned to engage the upper end 28 of the second upper arm 16 and the lower end 34 of the second lower arm 14, respectively. As such, the first arm pockets 45, 46 maintain the position of the first pair of arms 12, 14 and first hinge assembly 36 relative to the sleeve 44. The second arm pockets 47, 48 similarly maintain the position of the second pair of arms 16, 18 and second hinge assembly 40 relative to the sleeve 44.

The first arm pockets 45, 46 are formed by sewing a continuous length of a first backing 49 onto the sleeve 44 and sewing two shorter lengths of first upper and lower coverings 50, 51 onto the first backing 49 and sleeve 44. The length of the first upper covering 50 corresponds to the length of the upper end 20, while the length of the first lower covering 51 corresponds to the length of the lower end 26. A first lower opening 52 is maintained in the first upper seam 53 joining the first upper covering 50 to the first backing 49 and sleeve 44. The first lower opening 52 receives the upper end 20 of the first upper arm 12. A first upper opening 54 is maintained in the first lower seam 55 joining the first lower covering 51 to the first backing 49 and sleeve 44. The first upper opening 54 receives the lower end 26 of the first lower arm 14. The majority of the first backing 49 is positioned behind the upper and lower ends 20, 26. However, a first central section 56 of the first backing 49 is positioned behind the overlapping lower and upper ends 22, 24. The first central section 56 is defined herein as being included within the first hinge assembly 36. The first backing 49 and first upper and lower coverings 50, 51 are formed from a fabric which is as flexible as the material of the sleeve 44, but which is substantially non-stretchable The second arm pockets 47, 48 are likewise formed by sewing a continuous length of a second backing 57 onto the sleeve 44 and sewing two shorter lengths of second upper and lower coverings 58, 59 onto the second backing 57 and sleeve 44. The length of the second upper covering 58 corresponds to the length of the upper end 28, while the length of the second lower covering 59 corresponds to the length of the lower end 34. A second lower opening 60 is maintained in the second upper seam 61 joining the second upper covering 58 to the second backing 57 and sleeve 44. The second lower opening 60 receives the upper end 28 of the second upper arm 16. A second upper opening 62 is maintained in the second lower seam 63 joining the second lower to the second backing 57 and sleeve 44. The second upper opening 62 receives the lower end 34 of the second lower arm 18. The majority of the second backing 57 is positioned behind the upper and lower ends 28, 34. However, a second central section 64 of the second backing 57 is positioned behind the overlapping lower and upper ends 34, 32. The second central section 64 is defined herein as being included within the second hinge assembly 40. The second backing 57 and second upper and lower coverings 58, 59 are formed from the same fabric as the first backing 49 and first upper and lower coverings 55, 51. Additional foam padding (not shown), such as condyle pads and the like, may be provided on the inside of the sleeve 44 positioned in correspondence with the first and second hinge assemblies 36, 40.

A plurality of circumferential straps 65, 66, 67, 68 are provided to secure the knee orthosis 10 to the knee and counterbalance rotation of the first and second hinge assemblies 36, 40. The circumferential straps 65, 66, 67, 68 are formed from a fabric which is flexible, but substantially non-stretchable. The circumferential strap 65 is an upper anterior strap which extends anteriorly between the upper ends 20, 28 of the first and second upper arms 12, 16, respectively, and has an orientation substantially perpendicular to the longitudinal axis of the sleeve 44. The upper anterior strap 65 is secured by attaching one end 69 of the strap 65 to the sleeve 44 adjacent to the upper end 28 and threading the other end 70 of the strap 65 through a rigid strap loop 71 fixedly attached to the sleeve 44 adjacent to the upper end 20. The end 70 of the strap 65 is fitted with a releasable fastener and the strap 65 has a mid-section 72 which is correspondingly fitted with a cooperative releasable fastener. The cooperative releasable fasteners of the end 70 and mid-section 72 are preferably conventional releasable hook and loop fasteners, respectively, commercially available under the trade name "VELCRO". The length of the strap 65, is adjustable by overlapping the end 74 and the mid-section 72, selectively positioning the end 70 at a paint on the mid-section 72, and releasably fastening the end 70 to the mid-section 72 at the selected point.

The circumferential strap 66 is an upper posterior strap which has a construction substantially similar to that of the upper anterior strap 65, but which extends posteriorly between the upper ends 20, 28 of the first and second upper arms 12, 16, respectively. The upper posterior strap 66 has a substantially perpendicular orientation relative to the longitudinal axis of the sleeve 44 and is adjustably secured in substantially the same manner as described above with respect to the upper anterior strap 65. The circumferential strap 67 is a lower posterior strap which has a construction substantially similar to that of the upper anterior strap 65, but which extends posteriorly between the lower ends 26, 34 of the first and second lower arms 14, 18, respectively. The lower posterior strap 67 is oriented and adjustable secured in substantially the same manner as the upper anterior strap 65. The circumferential strap 68 is a lower anterior strap which has a construction substantially similar that of the upper anterior strap 65, but which extends anteriorly between the lower ends 26, 34 of the first and second lower arms 14, 18, respectively. The lower anterior strap 68 is oriented and adjustably secured in substantially the same manner as the upper anterior strap 65. Although not shown, it is apparent to the skilled artisan that one or more of the circumferential straps 65, 66, 67, 68 can alternatively be designed to circumscribe the entire sleeve 44, rather than only the anterior or posterior portion of the sleeve 44.

The knee orthosis 10 is further provided with a patellar tracking assembly which comprises a tracking guide 73, a compression plate 74, a counterbalance connector 76, a first tension strap 78, a second tension strap 80, and a tension strap mount 82. The tracking guide 73 and compression plate 74 are cooperatively positioned adjacent to a patellar opening 84 formed in the anterior side of the sleeve 44. The patellar opening 84 is shaped in correspondence with the periphery of a patella. A guide pocket 86 is sewn into the fabric of the sleeve 44 adjacent to the patellar opening 84. The guide pocket 86 and tracking are correspondingly arcuately configured with the tracking guide 73 fitted into and retained within the guide pocket 86. The tracking guide 73 is formed from a flexible material such as a neoprene foam and is preferably devoid of any right-angle edges, having a substantially rounded cross section, for the comfort of the user. In general, the material of the tracking guide 73 is substantially less rigid than the material of the compression plate 74 described hereafter, yet is substantially thicker, more dense, less compressible, and less stretchable than the material of the sleeve 44.

The compression plate 74 has an arcuate anterior profile substantially corresponding to that of the tracking guide 73 and has a relatively thin sheet-like elevational profile which bows slightly outward toward its middle to conform to the contour of the knee when the knee is in a position of substantially full extension as described hereafter. The compression plate 74 is generally constructed from a relatively rigid material, such as a metal or a plastic, e.g., nylon. The compression plate 74 is positioned against the anterior face 88 of the tracking guide 73 in overlapping engagement with the tracking guide 73 and the overlying guide pocket 86.

The counterbalance connector 76 connects the compression plate 74 to the second hinge assembly 40 in a substantially non-releasable and non-adjustable manner. The counterbalance connector 76 of the present embodiment is a connector strap constructed from a fabric which is flexible, but substantially non-stretchable. The connector 76 is substantially permanently attached to the compression plate 74 by threading an end 97 of the connector strap 76 through a middle strap slot 96 of the compression plate 74 and sewing the end 97 back onto of the connector strap 76. The middle strap slot 96 passes through the compression plate 74 at the longitudinal midpoint of the compression plate 74. The opposite end 98 of the connector strap 76 is substantially permanently attached to the second hinge assembly 40 by stitching which secures the end 98 to the second central section 64 of the second backing 57 behind the lower end 30 of the second upper arm 16, wherein the second central section 64 is substantially independent of movement of the second upper and lower arms 16, 18.

Although a preferred embodiment of the counterbalance connector 76 is described above and shown in the drawing, it is understood that the present invention is not limited to a specific embodiment of the counterbalance connector. The present invention encompasses counterbalance connectors having alternate connective structures or locations of connection within the purview of the skilled artisan which maintain a static counter force on the compression plate 74 in a direction opposite the first hinge assembly 36 and opposing the tension force of the first and second tension straps 78, 80 described hereafter. For example, the counterbalance connector may be a connector strap having one end attached to the compression plate 74 in substantially the same manner as described above but having the opposite end attached to a different component of the second hinge assembly 40 such as the lower end 30 of the second upper arm 16, the upper end 32 of the second lower arm 18, or the hinge pivot 42. The counterbalance connector may alternately be a fastener such as a rivet or screw which fastens the compression plate 74 directly to a location on the orthosis 10 at or proximal, preferably anterior, to the second hinge assembly 40. In yet another alternative, the counterbalance connector may be a connector strap having one end attached to the compression plate 74 in substantially the same manner as described above, but having the opposite end looped from the compression plate 74 posteriorly around the orthosis to the fist hinge assembly 36 and attached at or proximal thereto. This embodiment of the counterbalance connector has particular utility where the orthosis includes the first upper and lower arms 12, 14 and first hinge assembly 36, but excludes the second upper and lower arms 16, 18 and second hinge assembly 40.

The first and second tension straps 78, 80, like the connector strap 76, are constructed from a fabric which is flexible, but substantially non-stretchable. The first and second tension straps 78, 80 are each connected to the compression plate 74 utilizing upper and lower strap slots 99, 100, respectively, which pass through opposite upper and lower ends 102, 104 of the compression plate 74. The first and second tension straps 78, 80 are also each connected to the first hinge assembly 36 utilizing the tension strap mount 82 included in the first hinge assembly 36. The tension strap mount 82 comprises a mount pivot 106 and a mounting plate 108 having upper and lower strap slots 110, 112. The mounting plate 108 has a substantially rigid sheet-like construction similar to that of the compression plate 74. The mounting plate 108 is rotatably connected to the first-hinge assembly 36 by the mount pivot 106 which rotationally engages the upper end 24 of the first lower arm 14 at a point substantially offset from the hinge pivot 38 of the first hinge assembly 36. The mount-pivot 106 shown herein is a conventional river positioned within cooperatively aligned apertures 113 formed through the mounting plate 108 and upper end 24. It is apparent, however, that alternate pivots within the purview of the skilled artisan, such as threaded screws and the like, may be utilized in the knee orthosis 10 and fall within the scope of the present invention.

The first tension strap 78, alternately termed the upper tension strap, is substantially permanently attached to the compression plate 74 by threading an end 114 of the first tension strap 78 through the upper strap slot 99 of the compression plate 74 and sewing the end 114 back onto the first tension strap 78. The first tension strap 78 is opposingly connected to the first hinge assembly 36 in a releasable manner by threading the opposite end 115 of the first tension strap 78 through the upper strap slot 110 of the mounting plate 108. Thus, the first tension strap 78 extends anteriorly between the upper strap slot 110 of the mounting plate 108 and the upper strap slot 99 of the compression plate 74. The end 115 is fitted with a releasable fastener and a mid-section 116 of the first tension strap 78 is fitted with a cooperative releasable fastener wherein the cooperative releasable fasteners are preferably conventional releasable hook and loop fasteners commercially available under the trade name "VELCRO". The length of the first tension strap 78 is adjustable by overlapping the end 115 and the mid-section 116, selectively positioning the end 115 at a point on the mid-section 116, and releasably fastening the end 115 to the mid-section 116 at the selected point.

The second tension strap 80, alternately termed the lower tension strap, is substantially permanently attached to the compression plate 74 by threading an end 118 of the second tension strap 80 through the lower strap slot 100 of the compression plate 74 and sewing the end 118 back onto of the second tension strap 80. The second tension strap 80 is opposingly connected to the first hinge assembly 36 in a releasable manner by threading the opposite end 119 of the second tension strap 80 through the lower strap slot 112 of the mounting plate 108. Thus, the second tension strap 80 extends anteriorly between the lower strap slot 112 of the mounting plate 108 and the lower strap slot 100 of the compression plate 74. The end 119 is fitted with a releasable fastener and a mid-section 120 of the second tension strap 80 is fitted with a cooperative releasable fastener, wherein the cooperative releasable fasteners are preferably conventional releasable hook and loop fasteners commercially available under the trade name "VELCRO". The length of the second tension strap 80 is adjustable by overlapping the end 119 and the mid-section 120, selectively positioning the end 119 at a point on the mid-section 120, and releasably fastening the end 119 to mid-section 120 at the selected point.

It is apparent from the above-recited disclosure that the first and second tension straps 78, 80 provide a connection between the first hinge assembly 36 and the compression plate 74. The connection points 99, 100, 110, 112 move relative to the hinge pivots 38, 42 during operation of the knee orthosis 10 which enables the desired utility of the knee orthosis as described below.

Figure 6:
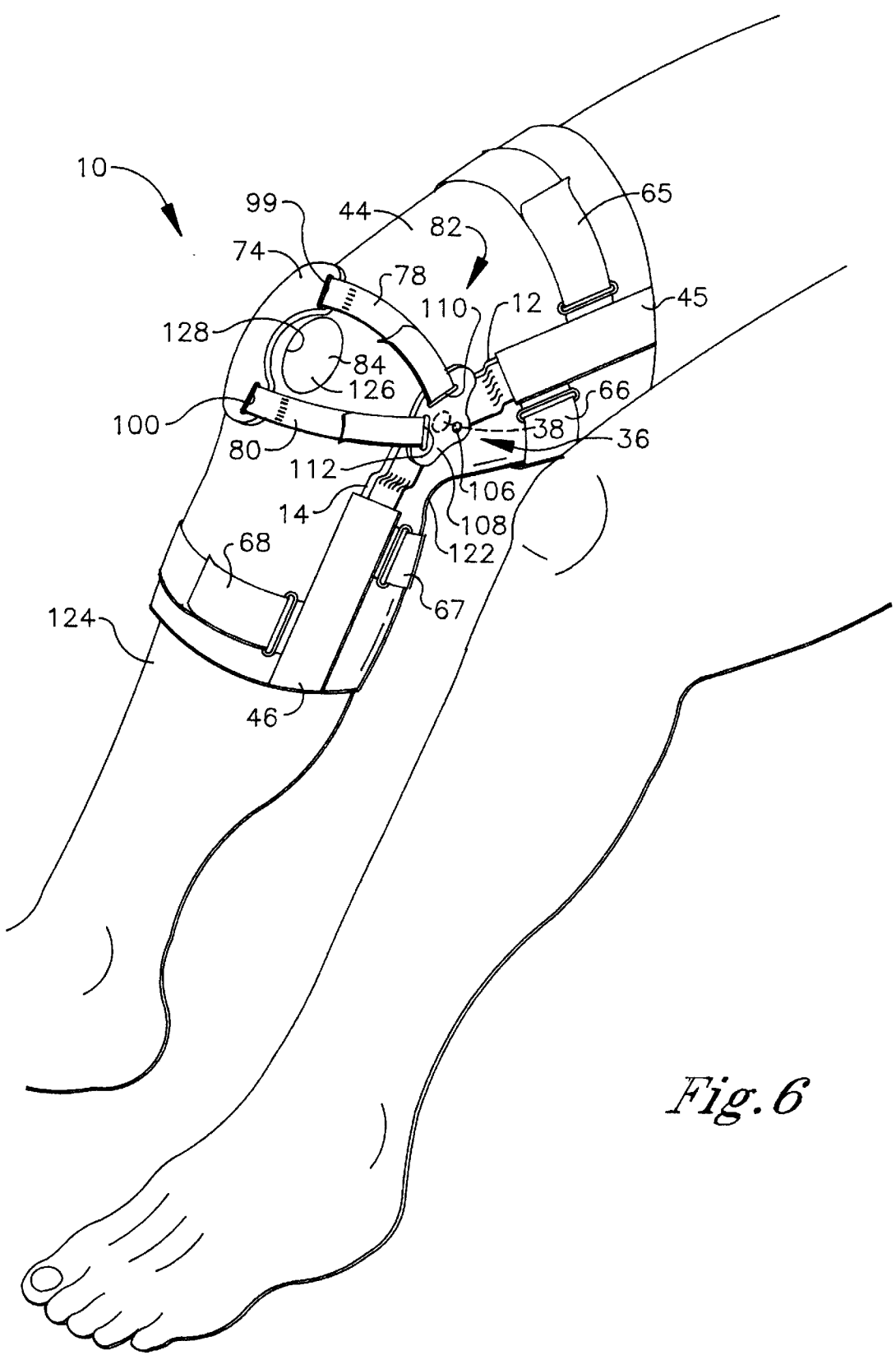
FIG. 6 is a perspective view of the knee orthosis of FIG. 1 operatively positioned an the knee of a user with the knee in the flexion position.

Operation of the knee orthosis 10 is described with continuing reference to FIGS. 1–5 and further reference to FIG. 6. The knee orthosis 10 is positioned on a knee 122 for which patellar stabilization is desired by pulling the sleeve 44 over the leg 124 until the patellar opening 84 circumscribes the patella 126. If one or more condyle pads (not shown) are utilized inside the sleeve 44, they are also appropriately positioned between the sleeve 44 and the condyles of the knee 122. The user manually positions the tracking guide 73 at the lateral side of the femoral head 128 adjacent to the patella 126 and trochlea (not shown behind the patella 126) taking care to insure that the tracking guide 73 does not overlap the patella 126. The user tightens the circumferential straps 65, 66, 67, 68 in a desired sequence while the knee 122 is in substantially full extension. The user then flexes the knee 122 at an angle of about 45° from full extension while maintaining the position of the tracking guide 73 at the lateral side of the femoral head 128 and tightens the first and second tension straps 78, 80 at a selected strap length which exerts a desired tension force on the compression plate 74. The strap length is preferably maintained fixed during range of motion movement of the knee 122, but can be readjusted if needed by interrupting the range of motion movement and tightening or loosening the first or second tension straps 78, 80 to a desired degree while the knee, orthosis 10 remains in place on the knee 122.

When the user performs range of motion movement on the knee 122, the knee orthosis 10 remediates existing patello-femoral joint disorders or precludes potential disorders by maintaining accurate patellar tracking of the trochlear groove to substantially prevent patellar subluxation or dislocation. Specifically, the first and second tension straps 78, 80 apply a tension force to the compression plate 74, which responds to the tension force by exerting a posteriorly-directed force against the tracking guide 73. Accordingly, the tension force presses and retains the tracking guide 73 in a self-adjusting position against the lateral side of the femoral head 128 with the face of the tracking guide 73 adjoining, but not overlapping, the adjacent edge of the patella 126. The position of the tracking guide 73 enforces a desired patellar track by maintaining the patella 126 in the underlying trochlear groove and preventing the patella 126 from migrating in a lateral direction out of the trochlear groove when the knee 122 moves through its normal range of motion. By not overlapping the patella 126, the tracking guide 73 also substantially avoids radial compression of the patella 126 which would undesirably tend to inhibit normal range of motion of the knee 122 and cause pain to the user.

An advantageous feature of the knee orthosis 10 is the ability to self-adjust in response to changes in the position of the knee 122. In particular, the position of the tracking guide 73 relative to the patella 126 and the tension force which presses the tracking guide 73 against the femoral head 128 are automatically self-adjusting as a function of the degree of flexion or extension of the knee 122. When the knee 122 approaches a position of full flexion, the tracking guide 73 is displaced away from the patella 126 and the force of the tracking guide 73 against the femoral head 128 diminishes. However, when the knee 122 approaches a position of full extension, the tracking guide 73 is displaced toward the patella 126 and the force of the tracking guide 73 against the femoral head 128 increases. Accordingly the tracking guide 73 is more securely retained against the femoral head 128 relatively proximal to the patella 126 when the risk of patellar subluxation or dislocation is greater, i.e., generally during the last 15° to 30° of knee extension, and less securely retained against the femoral head 128 relatively distal from the patella 126 when the risk of patellar subluxation or dislocation is least, i.e., during substantial knee flexion.

The self-adjusting position and compression features of the orthosis 10 are illustrated with reference to FIGS. 7–10. Referring initially to FIG. 7, the knee orthosis 10 is mounted on the knee 122 with the orthosis 10 and the knee 122 in corresponding positions of substantially full extension. As such, the alignment angle β of the first upper and lower arms 12, 14 at substantially full extension is shown as 180° for purposes of illustration. In practice, the alignment angle β at substantially full extension may encompass angles less than 180° to about 170° since it is often desirable to limit full extension of the knee 122 to somewhat less than 180° for treatment purposes. Although not shown in figure 7, the second upper and lower arms 16, 18 also have an alignment angle substantially equal to the alignment angle β of the first upper and lower arms 12, 14. The first upper and lower arms 12, 14 and hinge pivot 38 are aligned along a pivot reference axis shown as a vertical dashed line designated 129. The connection points 110, 112 of the first and second tension straps 78, 80 on the mounting plate 108 are also aligned with the hinge pivot 38 along the pivot reference axis 129.

Figure 8:
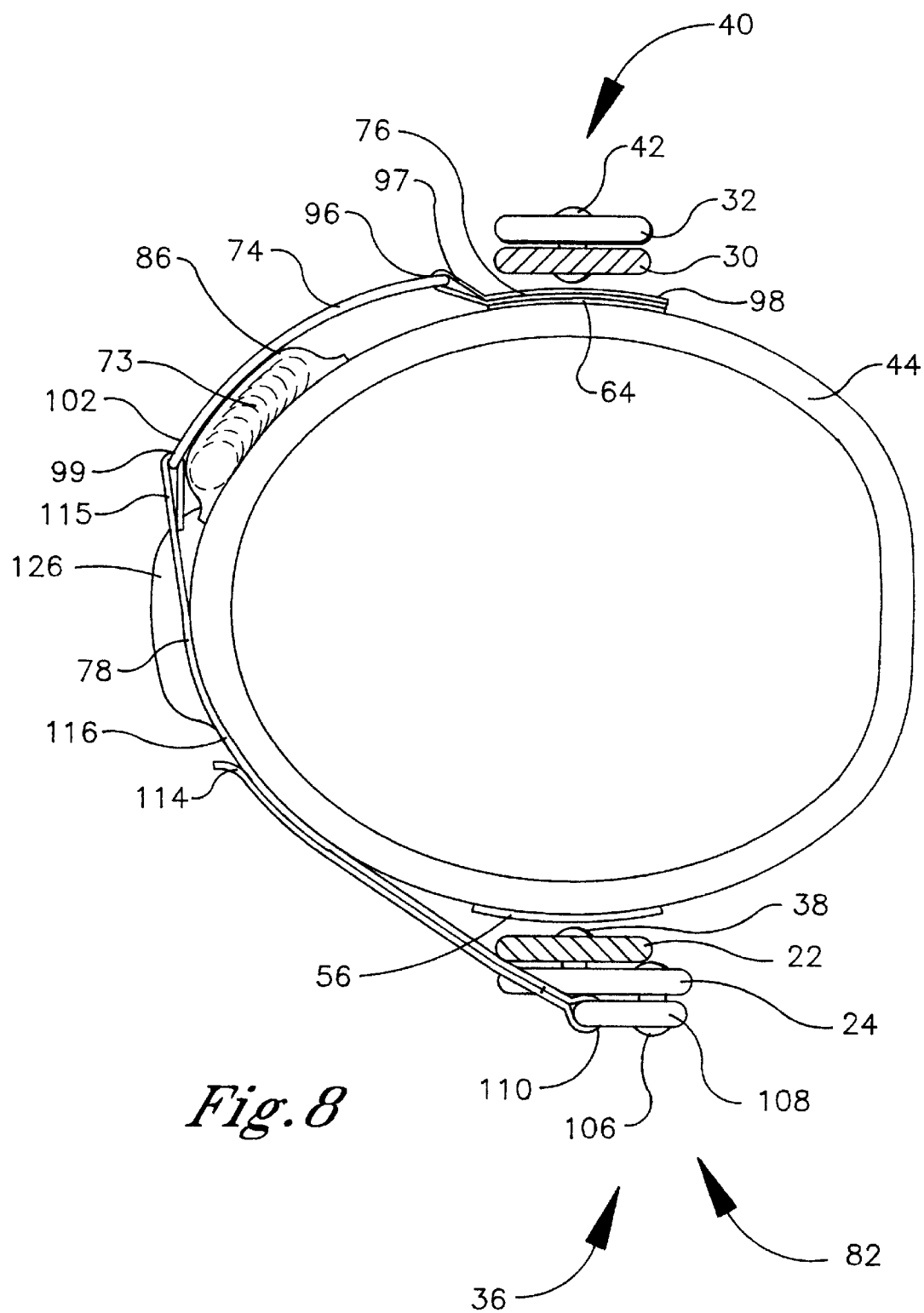
FIG. 8 is a top sectional view of the knee orthosis of FIG. 7 having the arm pockets and circumferential straps omitted for clarity of illustration.

Referring to FIG. 8, the connection point 99 of the first tension strap 78 is positioned relatively proximal to the surface of the knee 122 at the compression plate 74. Although not shown in FIG. 8, the connection point 100 of the second tension strap 80 is also positioned relatively proximal to the surface of the knee 122 at the compression plate 74. The relationship between the knee orthosis 10 and knee 122 is in part attributable to the elevational profile of the compression plate 74 as noted above, which is constructed to conform the contour of the knee 122 when the knee orthosis 10 and knee 122 are in positions of substantially full extension. The configuration of the knee orthosis 10 at substantially full extension, and in particular the relative positioning of the connection points 99, 100 and opposing connection points 110, 112, places the tracking guide 73 or compression plate 74 relatively proximal to the patella 126 which has an elevated profile in the extension position. Relatively large segments of the first and second tension straps 78, 80 engage the knee 122 as the first and second tension straps 78, 80 extend from the connection points 99, 100 to the connection points 110, 112, respectively, when the knee orthosis 10 is in full extension, causing the first and second tension straps 78, 80 to become more taut and increasing the tension force the first and second tension straps 78, 80 exert on the compression plate 74.

Referring to FIG. 9, the knee orthosis and knee 122 are rotated from the positions of substantially full extension shown in FIG. 7 to positions of flexion. As such, the alignment angle β of the first upper and lower arms 12,14 is decreased from about 180° to, about 90°. Although not shown in FIG. 9, the alignment angle of the second upper grid lower arms 16, 18 is likewise decreased to about 90°. The hinge pivot 38 remains aligned with the pivot reference axis 129, but the upper end 20 of the first upper arm 12 and the lower end 26 of the first lower arm 14 extend posteriorly away from the pivot reference axis 129 due to rotational displacement thereof. Rotation of the lower end 22 of the first upper arm 12 and the upper end 24 of the first lower arm 14 anteriorly displaces the connection points 110, 112 of the first and second tension straps 78, 80 on the mounting plate 108 relative to the hinge pivot 38 and pivot reference axis 129. Anterior displacement of the connection points 110, 112 causes corresponding displacement of the connection points 99, 100, drawing, the tracking guide 73 and compression plate 74 away from the patella 126.

Figure 10:
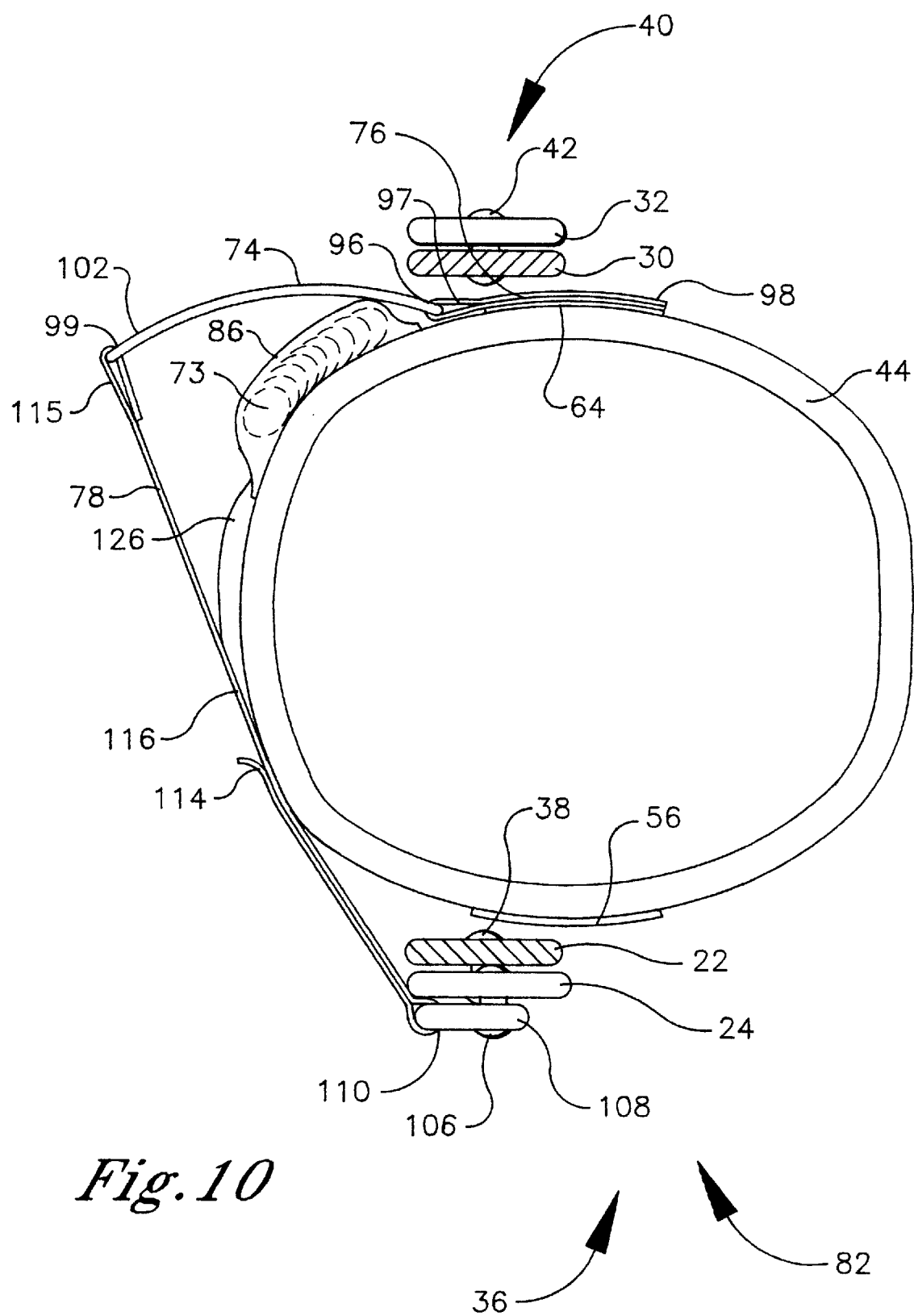
FIG. 10 is a top sectional view of the knee orthosis of FIG. 9 having the arm pockets and circumferential straps omitted for clarity of illustration.

Referring to FIG. 10, the connection point 99 of the first tension strap 78 is drawn radially outward away from the surface of the knee 122 at the compression plate 74. Although not shown in FIG. 10, the connection point 100 of the second tension strap 80 is also drawn radially outward away from the surface of the knee 122 at the compression plate 74. This relationship between the knee orthosis 10 and knee 122 is in part attributable to the relatively rigid material of the compression plate 74 which does not permit the compression plate 74 to flex in correspondence with alignment angle β when the knee orthosis 10 and knee 122 are in positions of flexion. The configuration of the knee orthosis 10 at flexion, and in particular the relative positioning of the connection paints 99, 100 and opposing connection points 110, 112, places the tracking guide 73 and compression plate 74 relatively distal to the patella 126 which has a relatively flat profile in the flexion position. Relatively small segments of the first and second tension straps 78, 80 engage the knee 122 as the first and second tension straps 78, 80 extend from the connection points 99, 100 to the connection points 110, 112, respectively, when the knee orthosis 10 is in flexion causing the first and second tension straps 78, 80 to become more slack decreasing the tension force the first and second tension straps 78, 80 exert on the compression plate 74. In an alternate embodiment not riot shown, a limited portion of the compression plate 74 proximal to the ends 102, 104 may be constructed from a somewhat more flexible material or otherwise provided with a hinge to enable some flexion of the ends 102, 104 of the compression plate 74 around the radial curvature of the knee 122 to reduce the protrusion of the ends 102, 104 from the knee 122 during flexion of the knee 122. However, it is preferable that the compression plate 74 be substantially rigid proximal to the middle strap slot 96 and substantially inflexible with respect to the direction of the alignment angle β.

Referring to FIGS. 11 and 12, an alternate embodiment of a knee orthosis is shown and generally designated 130. Components common to both knee orthoses 10 and 130 are designated by the same reference characters. The knee orthosis 130 is substantially the same as the knee orthosis 10 shown in FIGS. 1–10 except that upper and lower anterior cuffs 132, 134, rather than an elastic sleeve, are employed along with posterior circumferential straps 136, 138, 140, 142 to secure the knee orthosis 130 to the knee. The tracking guide 73 is fixably secured to the compression plate 74 by overmolding, an adhesive or other conventional securing means. The connector strap 76 is secured to the second hinge assembly by means of an independently rotatable mounting plate 144 which is rotatably connected to the upper end 32 as shown, or is alternatively connected to the lower end 30 or hinge pivot 38 (not shown). The mounting plate 144 is similar in construction to the mounting plate 108. The cuffs 132, 134 are substantially more rigid or stiffened than the elastic sleeve, being formed from one or more of the following types of materials metals, fiberglass, graphite, resins, plastics, composites, stiffened foams, and the like. The upper cuff 132 and upper arms 12, 16 as well as the lower cuff 134 and lower arms 14, 18 are shown as being separate and distinct structures, with the arms 12, 14, 16, 18 being attached to the cuffs by brackets 146. It is apparent to the skilled artisan, however, that the upper cuff 132 can be integrally formed with the upper arms 12, 16 from a common material as a single structure and that the lower cuff 134 can likewise be integrally formed with the lower arms 14, 18 from a common material as a single structure within the scope of the present invention.

The embodiments of the knee orthoses 10, 130 are configured to substantially prevent lateral patellar subluxation or dislocation of the patella 126 by positioning the tracking guide 73 and compression plate 74 against the lateral side of the femoral head 128 and connecting the first and second tension straps 78, 80 to the first hinge assembly 36. Although most patellar subluxation or dislocation is lateral, it is apparent to the skilled artisan that the present knee orthosis can be readily reconfigured in a manner not shown, but within the scope of the present invention, to substantially prevent medial patellar subluxation or dislocation simply by reversing the positions of the components of the patellar tracking assembly. Specifically, the compression plate and tracking guide can be repositioned against the medial side of the femoral head while the first and second tension straps are reconnected to the second hinge assembly.

In the above-recited embodiments 10, 130 of the present invention, the tracking guide 73 and compression plate 74 have been shown and described as two functionally cooperative, but structurally discrete elements which physically engage one another. However, it is understood that the tracking guide 73 and compression plate 74 or not limited to the specific embodiment shown herein. It is apparent that these two elements can alternatively be integrally constructed as a single element which performs the same function in the same manner to achieve the same result as the separate tracking guide and compression plate. As such, the term compression member is used generally herein to refer to one or more elements which alone or collectively are maintained in position at the femoral head adjacent to the patella by connection to the first and second tension straps to provide a patellar tracking guide in accordance with the present teaching.

Referring to FIG. 13, an alternate embodiment of a patellar tracking assembly and an associated first hinge assembly 150 is shown which can be employed in either knee orthosis 10 or 130. Components of FIG. 13 common to FIGS. 1–12 are designated by the same reference characters. The first hinge assembly 150 is of the type disclosed in U.S. Pat. No. 5,807,294, wherein the hinge pivot has separate pivot elements 152, 154 for the lower end 22 of the first upper arm 12 and the upper end 24 of the first lower arm 14, respectively. Teeth 156, 158 are provided on the lower and upper ends 22, 24, respectively, which in association with the pivot elements 152, 154 enable cooperative rotation the upper and lower arms 12, 14. A back hinge plate 160 is positioned behind the lower and upper ends 22, 24 to retain the pivot elements 152, 154 and shield the user from the moving parts of the first hinge assembly 150. A front plate (not shown) may also be provided in front of the lower and upper ends 22, 24.

The patellar tracking assembly of FIG. 13 comprises a relatively rigid mounting plate 162 having upper and lower strap slots 110, 112 for the first and second tension straps (not shown) which are constructed substantially the same as the first and second tension straps 78, 80 of FIGS. 1–12. The mounting plate 162 has an integral rigid hinge engagement member 164 which extends posteriorly between the lower end 22 and the upper end 24. The hinge engagement member 164 is provided with teeth 166 which intermesh with the teeth 156, 158. When the knee is flexed from a position of full extension, the upper and lower arms 12, 14 cooperatively rotate, causing the lower and upper ends 22, 24 to urge out the hinge engagement member 164 and anteriorly displace the connection points 110, 112 of the first and second tension traps relative to the hinge pivot 152, 154. Accordingly, the tension force of the first and second tension straps diminishes when the knee approaches a position of flexion and increases when the knee approaches a position of full extension. Likewise, the tracking guide and compression plate (not shown) are drawn away from the patella when the knee approaches a position of flexion and drawn toward the patella when the knee approaches a position of full extension in a similar manner as described above with reference to the knee orthosis 10.

Referring to FIG. 14, another alternate embodiment of a patellar tracking assembly and an associated first hinge assembly 170 is shown which can alternatively be employed in either knee orthosis 10 or 130. Components of FIG. 14 common to FIGS. 1–13 are designated by the same reference characters. The first hinge assembly 170 has a hinge pivot with separate pivot elements 152, 154 for the lower end 22 of the first upper arm 12 and the upper end 24 of the first lower arm 14, respectively, which enable rotation of the upper and lower arms 12, 14. A back hinge plate 160 is positioned behind the lower and upper ends 22, 24 to retain the pivot elements 152, 154 and shield the user from the moving parts of the first hinge assembly 170.

The patellar tracking assembly of FIG. 14 comprises an upper mounting plate 172 and a lower mounting plate 174. The upper and lower mounting plates 172, 174 are fixably attached to the lower and upper ends 22, 24 of the upper and lower arms 12,14, respectively, and are rotatable about the pivot elements 152, 154 in cooperation with the upper and lower arms 12, 14. The upper and lower mounting plates 172, 174 are identically disc-shaped and each has a continuous circumferential groove 175, 176 and a plurality of shaped slots 177, 178 formed at spaced intervals along the circumference. The patellar tracking assembly further comprises a first tension strap 180 and a second tension strap 182 both in the form of a flexible wire or cable. The first and second tension straps 180, 182 each connect at one end to the compression plate (not shown) and each has a nub 184, 186 on its opposite end which can be received in the circumferential groove 175, 176 and retained by one of the selected shaped slots 177, 178, respectively.

The first and second-tension straps 180, 182 function in substantially the same manner as the first and second tension straps 78, 80 of FIGS. 1–12. When the knee is flexed from a position of full extension as shown in FIG. 14, the upper and lower arms 12,14 rotate, anteriorly displacing the connection paints 177, 178 of the first and second tension straps 180, 182 relative to the hinge pivot 152, 154 and causing the lower and upper ends 22, 24 to play out the first and second tension straps 180, 182 along the circumferential grooves 175, 176 with the upper and lower mounting plates 172, 174 each acting in the manner of a pulley. Accordingly, the tension force of the first and second tension straps 180, 182 diminishes when the knee approaches a position of flexion and increases when the knee approaches a position of full extension. Likewise, the tracking guide and compression plate (not shown) are drawn away from the patella when the knee approaches a position of flexion and drawn toward the patella when the knee approaches a position of full extension in a similar manner as described above with reference to the knee orthosis 10. It is further noted that the effective length of the first and second tension straps 180, 182 is adjustable by selectively repositioning the nubs 184, 186 in alternate shaped slots 177, 178 as desired.

While the forgoing preferred embodiments of the invention have been described and shown, it is understood chat alternatives and modifications, such as those suggested and others, may be made thereto and fall within the scope of the invention.

We claim:

1. An orthosis mountable on a knee having a femoral head and patella to maintain proper tracking of the patella relative to the femoral head during movement of the knee, said orthosis comprising:

an upper arm and a lower arm positionable about the knee;

a hinge assembly positioned between said upper arm and said lower arm and positionable at the knee to one side of the patella, said hinge assembly having a hinge pivot wherein said upper arm and said lower arm are rotatable about said hinge pivot to transition between a flexion position and an extension position;

a tension strap connected to said hinge assembly at a first connection point;

a compression member positionable at the femoral head adjacent to the patella, said tension strap connected to said compression member at a second connection point to apply a tension force to said compression member, wherein said tension force increases when said upper and lower arms rotatably transition from said flexion position to said extension position and decreases when said upper and lower arms rotatably transition from said extension position to said flexion position; and means for applying a counter force to said compression member opposing said tension force.

2. The orthosis of claim 1 wherein said hinge assembly includes a lower end of said upper arm and an upper end of said lower arm, wherein said hinge pivot rotationally engages said lower end and said upper end.

3. The orthosis of claim 2 wherein said hinge assembly further comprises a tension strap mount connected to said lower end or said upper end and wherein said first connection point is positioned on said tension strap mount.

4. The orthosis of claim 3 wherein said tension strap mount includes a mount pivot and a mounting plate, wherein said mount pivot is spatially offset from said hinge pivot and rotatably connects said mounting plate to said lower or upper end.

5. The orthosis of claim 1 wherein said counter force applying means is a counterbalance connector connected to said compression member and oriented counter to said tension strap.

6. The orthosis of claim 1 wherein said compression member comprises a tracking guide engagable with the knee at the femoral head adjacent to the patella and a compression plate in overlying engagement with said tracking guide.

7. The orthosis of claim 6 wherein said compression plate is formed from a substantially more rigid material than said tracking guide and wherein said second connection point is on said compression plate.

8. The orthosis of claim 1 wherein said tension strap is a first tension strap and said orthosis further comprises a second tension strap connected to said hinge assembly at a third connection point and to said compression member at a fourth connection point, said second tension strap being positioned below said first tension strap.

9. The orthosis of claim 1 further comprising a substantially flexible tubular sleeve retaining said upper and lower arms.

10. The orthosis of claim 1 further comprising a stiffened upper cuff retaining said upper arm and a stiffened lower cuff retaining said lower arm.

11. The orthosis of claim 1 wherein said upper arm is a first upper arm, said lower arm is a first lower arm and said hinge assembly is a first hinge assembly, said orthosis further comprising a second upper arm and a second lower arm and a second hinge assembly positioned between said second upper arm and said second lower arm and positionable at the knee to the opposite side of the patella from said first hinge assembly.

12. The orthosis of claim 11 further comprising a connector strap connectively extending between said compression member and said second hinge assembly.

13. An orthosis mountable on a knee having a femoral head and patella to maintain proper tracking of the patella relative to the femoral head during movement of the knee, said orthosis comprising:
    an upper arm and a lower arm positionable about the knee;
    a hinge assembly positioned between said upper arm and said lower arm and positionable at the knee to one side of the patella, said hinge assembly having a hinge pivot wherein said upper arm and said lower arm are rotatable about said hinge pivot to transition between a flexion position and an extension position;
    a tension strap connected to said hinge assembly at a first connection point; and
    a compression member positionable at the femoral head adjacent to the patella, said tension strap connected to said compression member at a second connection point to apply a tension force to said compression member, wherein said compression member is positionable more proximal to the patella when said upper and lower arms rotatably transition from said flexion position to said extension position and is positionable more distal to the patella when said upper and lower arms rotatably transition from said extension position to said flexion position; and
    means for applying a counter force to said compression member opposing said tension force.

14. The orthosis of claim 13 wherein said hinge assembly includes a lower end of said upper arm and an upper end of said lower arm, wherein said hinge pivot rotationally engages said lower end and said upper end.

15. The orthosis of claim 14 wherein said hinge assembly further comprises a tension strap mount connected to said lower end or said upper end and wherein said first connection point is positioned on said tension strap mount.

16. The orthosis of claim 15 wherein said tension strap mount includes a mount pivot and amounting plate, wherein said mount pivot is spatially offset from said hinge pivot and rotatably connects said mounting plate to said lower or upper end.

17. The orthosis of claim 13 wherein said counter force applying means is a counterbalance connector connected to said compression member and oriented counter to said tension strap.

18. The orthosis of claim 13 wherein said compression member comprises a tracking guide engagable with the knee at the femoral head adjacent to the patella and a compression plate in overlying engagement with said tracking guide.

19. The orthosis of claim 18 wherein said compression plate is formed from a substantially more rigid material than said tracking guide and wherein said second connection point is on said compression plate.

20. The orthosis of claim 13 wherein said tension strap is a first tension strap and said orthosis further comprises a second tension strap connected to said hinge assembly at a third connection point and to said compression member at a fourth connection point, said second tension strap being positioned below said first tension strap.

21. The orthosis of claim 13 further comprising a substantially flexible tubular sleeve retaining said upper and lower arms.

22. The orthosis of claim 13 further comprising a stiffened upper cuff retaining said upper arm and a stiffened lower cuff retaining said lower arm.

23. The orthosis of claim 13 wherein said upper arm is a first upper arm, said lower arm is a first lower arm and said hinge assembly is a first hinge assembly, said orthosis further comprising a second upper arm and a second lower arm and a second hinge assembly positioned between said second upper arm and said second lower arm and positionable at the knee to the opposite side of the patella from said first hinge assembly.

24. The orthosis of claim 23 further comprising a connector strap connectively extending between said compression member and said second hinge assembly.

25. An orthosis mountable on a knee having a femoral head and patella to maintain proper tracking of the patella relative to the femoral head during movement of the knee, said orthosis comprising:
    an upper arm and a lower arm positionable about the knee;
    a hinge assembly positioned between said upper arm and said lower arm and positionable at the knee to one side of the patella, said hinge assembly having a hinge pivot wherein said upper arm and said lower arm are rotatable about said hinge pivot to transition between a flexion position and an extension position;
    a tension strap connected to said hinge assembly at a first connection point; and
    a compression member positionable at the femoral head adjacent to the patella, said tension strap connected to said compression member at a second connection point to apply a tension force to said compression member, wherein said first connection point is posteriorly displaced relative to said hinge pivot when said upper and lower arms rotatably transition from said flexion position to said extension position and is anteriorly displaced when said upper and lower arms rotatably transition from said extension position to said flexion position; and means for applying a counter force to said compression member opposing said tension force.

26. An orthosis mountable on a knee having a femoral head and patella to maintain proper tracking of the patella relative to the femoral head during movement of the knee, said orthosis comprising:

a first upper arm and a first lower arm positionable about the knee;

a first hinge assembly positioned between said first upper arm and said first lower arm and positionable at the knee to one side of the patella, wherein said first upper arm and said first lower arm are rotatable about said first hinge assembly between a flexion position and an extension position;

a second upper arm and a second lower arm positionable about the knee;

a second hinge assembly positioned between said second upper arm and said second lower arm and positionable at the knee to the opposite side of the patella from said first hinge assembly, wherein said second upper arm and said second lower arm are rotatable about said second hinge assembly between said flexion position and said extension position;

a tension strap connected to said first hinge assembly at a first connection point;

a compression member positionable at the femoral head adjacent to the patella on the opposite side of the patella from said first hinge assembly and the same side of the patella as said second hinge assembly, said tension strap connected to said compression member at a second connection point to apply a tension force to said compression member, wherein said tension force increases when said first upper and lower arms rotatably transition from said flexion position to said extension position and decreases when said first upper and lower arms rotatably transition from said extension position to said flexion position; and a connector strap connectively extending between said compression member and said second hinge assembly in a counter orientation to said tension strap.

27. An orthosis mountable on a knee having a femoral head and patella to maintain proper tracking of the patella relative to the femoral head during movement of the knee, said orthosis comprising:

a first upper arm and a first lower arm positionable about the knee;

a first hinge assembly positioned between said first upper arm and said first lower arm and positionable at the knee to one side of the patella, wherein said first upper arm and said first lower arm are rotatable about said first hinge assembly between a flexion position and an extension position;

a second upper arm and a second lower arm positionable about the knee;

a second hinge assembly positionable between said second upper arm and said second lower arm at the knee to the opposite side of the patella from said first hinge assembly, wherein said second upper arm and said second lower arm are rotatable about said second hinge assembly between said flexion position and said extension position;

a tension strap connected to said first hinge assembly at a first connection point;

a compression member positionable at the femoral head adjacent to the patella on the opposite side of the patella from said first hinge assembly and the same side of the patella as said second hinge assembly, said tension strap connected to said compression member at a second connection point to apply a tension force to said compression member, wherein said compression member is positionable more proximal to the patella when said upper and lower arms rotatably transition from said flexion position to said extension position and is positionable more distal to the patella when said upper and lower arms rotatably transition from said extension position to said flexion position; and a connector strap connectively extending between said compression member and said second hinge assembly in a counter orientation to said tension strap.

28. An orthosis mountable on a knee having a femoral head and patella to maintain proper tracking of the patella relative to the femoral head during movement of the knee, said orthosis comprising:

an upper arm and a lower arm positionable about the knee;

a hinge assembly positioned between said upper arm and said lower arm and positionable at the knee to one side of the patella, said hinge assembly having a hinge pivot wherein said upper arm and said lower arm are rotatable about said hinge pivot to transition between a flexion position and an extension position;

a compression member including a tracking guide engagable with the knee at the femoral head adjacent to the patella and a compression plate in overlying engagement with said tracking guide, wherein said compression plate is formed from a more rigid material than said tracking guide;

a tension strap connected to said orthosis away from said compression member at a first connection point and connected to said compression plate at a second connection point, wherein said tension strap applies a tension force to said compression member in a first direction, said tension force increasing when said upper and lower arms rotatably transition from said flexion position to said extension position and decreasing when said upper and lower arms rotatably transition from said extension position to said flexion position; and means for applying a counter force to said compression member, wherein said counter force opposes said tension force in a second direction away from said first direction.

29. An orthosis mountable on a knee having a femoral head and patella to maintain proper tracking of the patella relative to the femoral head during movement of the knee, said orthosis comprising:

an upper arm and a lower arm positionable about the knee;

a hinge assembly positioned between said upper arm and said lower arm and positionable at the knee to one side of the patella, said hinge assembly including a hinge pivot, a lower end of said upper arm, an upper end of said lower arm, and a tension strap mount having a mount pivot and a mounting plate, wherein said mount pivot is spatially offset from said hinge pivot and rotatably connects said mounting plate to said lower or upper end and wherein said hinge pivot rotationally engages said lower end and said upper end such that said upper arm and said lower arm are rotatably about said hinge pivot to transition between a flexion position and an extension position;

a tension strap connected to said tension strap mount at a first connection point;

a compression member positionable at the femoral head adjacent to the patella, said tension strap connected to said compression member at a second connection point to apply a tension force to said compression member in a first direction, wherein said tension force increases when said upper and lower arms rotatably transition from said flexion position to said extension position and decreases when said upper and lower arms rotatably transition from said extension position to said flexion position; and means for applying a counter force to said compression member, wherein said counter force opposes said tension force in a second direction away from said first direction.

30. An orthosis mountable on a knee having a femoral head and patella to maintain proper tracking of the patella relative to the femoral head during movement of the knee, said orthosis comprising:

a first upper arm and a first lower arm positionable about the knee;

a first hinge assembly positioned between said first upper arm and said first lower arm and positionable at the knee to one side of the patella, said first hinge assembly having a hinge pivot wherein said upper arm and said lower arm are rotatably about said hinge pivot to transition between a flexion position and an extension position;

a tension strap connected to said first hinge assembly at a first connection point;

a compression member positionable at the femoral head adjacent to the patella on the opposite side of the patella from said first hinge assembly, said tension strap connected to said compression member at a second connection point to apply a tension force to said compression member, wherein said tension force increases when said upper and lower arms rotatably transition from said flexion position to said extension position and decreases when said upper and lower arms rotatably transition from said extension position to said flexion position;

a second upper arm and a second lower arm and a second hinge assembly positioned between said second upper arm and said second lower arm and positionable at the knee to the opposite side of the patella from said first hinge assembly; and a connector strap connectively extending between said compression member and said second hinge assembly.

31. An orthosis mountable on a knee having a femoral head and patella to maintain proper tracking of the patella relative to the femoral head during movement of the knee, said orthosis comprising:

an upper arm and a lower arm positionable about the knee;

a hinge assembly positioned between said upper arm and said lower arm and positionable at the knee to one side of the patella, said hinge assembly having a hinge pivot wherein said upper arm and said lower arm are rotatably about said hinge pivot to transition between a flexion position and an extension position;

a compression member including a tracking guide engagable with the knee at the femoral head adjacent to the patella and a compression plate in overlying engagement with said tracking guide, wherein said compression plate is formed from a more rigid material than said tracking guide;

a tension strap connected to said orthosis away from said compression member at a first connection point and connected to said compression plate at a second connection point, wherein said tension strap applies a tension force to said compression member in a first direction and said compression member is positionable more proximal to the patella when said upper and lower arms rotatably transition from said flexion position to said extension position and is positionable more distal to the patella when said upper and lower arms rotatably transition from said extension position to said flexion position; and means for applying a counter force to said compression member, wherein said counter force opposes said tension force in a second direction away from said first direction.

32. An orthosis mountable on a knee having a femoral head and patella to maintain proper tracking of the patella relative to the femoral head during movement of the knee, said orthosis comprising:

an upper arm and a lower arm positionable about the knee;

a hinge assembly positioned between said upper arm and said lower arm and positionable at the knee to one side of the patella, said hinge assembly including a hinge pivot, a lower end of said upper arm, an upper end of said lower arm, and a tension strap mount having a mount pivot and a mounting plate, wherein said mount pivot is spatially offset from said hinge pivot and rotatably connects said mounting plate to said lower or upper end and wherein said hinge pivot rotationally engages said lower end and said upper end such that said upper arm and said lower arm are rotatably about said hinge pivot to transition between a flexion position and an extension position;

a tension strap connected to said tension strap mount at a first connection point;

a compression member positionable at the femoral head adjacent to the patella, said tension strap connected to said compression member at a second connection point to apply a tension force to said compression member in a first direction, wherein said compression member is positionable more proximal to the patella when said upper and lower arms rotatably transition from said flexion position to said extension position and is positionable more distal to the patella when said upper and lower arms rotatably transition from said extension position to said flexion position; and means for applying a counter force to said compression member, wherein said counter force opposes said tension force in a second direction away from said first direction.

33. An orthosis mountable on a knee having a femoral head and patella to maintain proper tracking of the patella relative to the femoral head during movement of the knee, said orthosis comprising:

a first upper arm and a first lower arm positionable about the knee;

a first hinge assembly positioned between said first upper arm and said first lower arm and positionable at the knee to one side of the patella, said first hinge assembly having a hinge pivot wherein said upper arm and said lower arm are rotatably about said hinge pivot to transition between a flexion position and an extension position;

a tension strap connected to said first hinge assembly at a first connection point;

a compression member positionable at the femoral head adjacent to the patella on the opposite side of the patella from said first hinge assembly, said tension strap connected to said compression member at a second connection point to apply a tension force to said compression member, wherein said compression member is positionable more proximal to the patella when said upper and lower arms rotatably transition from said flexion position to said extension position and is positionable more distal to the patella when said upper and lower arms rotatably transition from said extension position to said flexion position;

a second upper arm and a second lower arm and a second hinge assembly positioned between said second upper arm and said second lower arm and positionable at the knee to the opposite side of the patella from said first hinge assembly; and a connector strap connectively extending between said compression member and said second hinge assembly.

34. A method for maintaining proper patellar tracking during range of motion movement of a knee comprising:

placing a compression member in engagement with a knee having a femoral head and a patella, wherein said compression member is positioned at a location on said femoral head adjacent to said patella and aligning said compression member with a desired dynamic patellar track;

performing a range of motion movement on said knee by moving said knee from a flexion position to an extension position or from an extension position to a flexion position;

connecting a tension strap to said compression member and extending said tension strap over said knee such that a segment of said tension strap having a segment length is in engagement with said knee;

increasing said segment length to tighten said tension strap and increase said tension force, thereby pressing said compression member against said femoral head when said knee approaches said extension position; and decreasing said segment length to slacken said tension strap and decrease said tension force when said knee approaches said flexion position.

35. A method for maintaining proper patellar tracking during range of motion movement of a knee comprising:

positioning an upper arm and a lower arm about a knee having a femoral head and patella;

positioning a hinge assembly between said upper arm and said lower arm at said knee to one side of said patella, wherein said upper arm and said lower arm are rotatable about said hinge assembly between a flexion position and an extension position;

placing a compression member in engagement with said knee at a location on said femoral head adjacent to said patella and aligning said compression member with a desired dynamic patellar track;

connecting a tension strap to a first connection point at said hinge assembly and to a second connection point at said compression member to apply a tension force to said compression member;

performing a range of motion movement on said knee by moving said knee from said flexion position to said extension position or from said extension position to said flexion position; and increasing said tension force by displacing said first connection point posteriorly with respect to said knee when said knee and said upper and lower arms transition from said flexion position to said extension position and decreasing said tension force by displacing said first connection point anteriorly with respect to said knee when said knee and said upper and lower arms transition from said extension position to said flexion position.

* * * * *